United States Patent
Lee et al.

(10) Patent No.: US 11,578,121 B2
(45) Date of Patent: Feb. 14, 2023

(54) ANTI-EGF LIKE DOMAIN MULTIPLE 6 (EGFL6) ANTIBODIES

(71) Applicants: TAIPEI MEDICAL UNIVERSITY, Taipei (TW); CHANGHUA CHRISTIAN MEDICAL FOUNDATION CHANGHUA CHRISTIAN HOSPITAL, Changhua (TW); NATIONAL RESEARCH INSTITUTE OF CHINESE MEDICINE, MINISTRY OF HEALTH AND WELFARE, Taipei (TW)

(72) Inventors: Yu-Ching Lee, Taipei (TW); Shiow-Lin Pan, Taipei (TW); Wei-Chun Huangfu, Taipei (TW); Tsui-Chin Huang, Taipei (TW); Po-Li Wei, Taipei (TW); Han-Li Huang, Taipei (TW); Chun-Chun Cheng, Taipei (TW); Cheng-Chiao Huang, Taipei (TW); Keng-Chang Tsai, Taipei (TW); Kun-Tu Yeh, Changhua (TW); Ting-Yi Sung, Taipei (TW); Fu-Ling Chang, Taipei (TW)

(73) Assignees: Taipei Medical University, Taipei (TW); Changhua Christian Medical Foundation Changhua Christian Hospital, Changhua (TW); National Research institute of Chinese Medicine, Ministry of Health and Welfare, Taipei (TW)

( * ) Notice: Subject to any disclaimer, the term of this patent is extended or adjusted under 35 U.S.C. 154(b) by 0 days.

(21) Appl. No.: 16/652,929

(22) PCT Filed: Sep. 28, 2018

(86) PCT No.: PCT/CN2018/108427
§ 371 (c)(1),
(2) Date: Apr. 1, 2020

(87) PCT Pub. No.: WO2019/062871
PCT Pub. Date: Apr. 4, 2019

(65) Prior Publication Data
US 2020/0239560 A1   Jul. 30, 2020

Related U.S. Application Data

(60) Provisional application No. 62/566,509, filed on Oct. 1, 2017.

(51) Int. Cl.
*A61K 39/395* (2006.01)
*C07K 16/22* (2006.01)
*C07K 16/00* (2006.01)
*A61K 39/00* (2006.01)

(52) U.S. Cl.
CPC ...... *C07K 16/22* (2013.01); *A61K 39/001131* (2018.08); *C07K 16/005* (2013.01); *A61K 2039/505* (2013.01); *C07K 2317/24* (2013.01); *C07K 2317/565* (2013.01); *C07K 2317/622* (2013.01)

(58) Field of Classification Search
None
See application file for complete search history.

(56) References Cited

FOREIGN PATENT DOCUMENTS

WO      2009057849 A1    5/2009
WO      WO-2017136807 A1 *  8/2017  ............ C07K 16/22

OTHER PUBLICATIONS

Carmeliet (Nature Medicine 9(6): 653-660, 2003).*
Mallbris et al. (J. Clin. Aesthet. Dermatol. 9(7): 13-15, 2016).*
Yeung et al. Genomics 62: 304-307, 1999.*
Wang et al. PLOS ONE 7(12): e52707, 2012.*
Kang et al. Int. J. Med. Sci. 17(10): 1320-1326, 2020.*
https://www.proteinatlas.org/ENSG00000198759-EGFL6/pathology, accessed on Jul. 14, 2022.*
Ewert et al., "Structure-Based Improvement of the Biophysical Properties of Immunoglobulin VH Domains with a Generalizable Approach," Biochemistry, 2003, vol. 42, pp. 1517-1528.
Januchowski. R. et al., Oncology Reports 32: 1981-1990, 2014.
Larimer. Benjimin M, "Identification of a Peptide from In vivo Bacteriophage Display with Homology to EGFL6: A Candidate Tumor Vasculature Ligand in Breast Cancer", J. Mol Biomark Diagn. 2014, 5(3): doi:10.4172/2155-9929.1000178.
Noh, Kyunghee, et al. Differential effects of EGFL6 on tumor versus wound angiogenesis. Cell reports, 2017, 21.10: 2785-2795.
Ronald J. Buckanovich et al., Journal of Clinical Oncology, 2007, vol. 25, No. 7, pp. 852-861.
Sidhu et al., "Constructing phage display libraries by oligonucleotide-directed mutagenesis," Dept. of Protein Engineering, Genentech, Inc., 1 DNA Way, South San Francisco, CA 94080. 2004.
Tsurushita et al., "Humanization of a chicken anti-IL-12 monoclonal antibody", JIM, vol. 295, pp. 1-19, 2004.
Wu, Binhua, et al. "Preparation and inhibition of proliferation and migration of human melanoma cells of monoclonal antibodies against human EGFL6 gene." 第十屆全國免疫學學術大會彙編 (2015).
Zilber et al., "NMR-Derived Model for a Peptide-Antibody Complex", Biochemistry, 1990, vol. 29, pp. 10032-10041.

* cited by examiner

*Primary Examiner* — Christine J Saoud
(74) *Attorney, Agent, or Firm* — Prosyla Group PC

(57) ABSTRACT

The invention relates to anti-EGF like domain multiple 6 antibody (anti-EGFL6 antibody) and cancer detection (or diagnosis) and treatment using the anti-EGFL6 antibody. The present invention creates anti-EGFL6 antibodies, particularly, a single-chain antibody fragments (scFv) and humanized antibody, which have ability in binding to EGFL6 and in inhibiting angiogenesis and cancer cell growth.

6 Claims, 8 Drawing Sheets

Specification includes a Sequence Listing.

(A)

(B)

(A)

(B)

(A)

(B)

SEQUENCE LISTING

```
<160> NUMBER OF SEQ ID NOS: 16

<210> SEQ ID NO 1
<211> LENGTH: 5
<212> TYPE: PRT
<213> ORGANISM: artificial sequence
<220> FEATURE:
<223> OTHER INFORMATION: synthetic peptide

<400> SEQUENCE: 1

Gly Asn Asp Lys Tyr
1               5

<210> SEQ ID NO 2
<211> LENGTH: 5
<212> TYPE: PRT
<213> ORGANISM: artificial sequence
<220> FEATURE:
<223> OTHER INFORMATION: synthetic peptide

<400> SEQUENCE: 2

Ser Gly Arg Tyr Gly
1               5

<210> SEQ ID NO 3
<211> LENGTH: 3
<212> TYPE: PRT
<213> ORGANISM: artificial sequence
<220> FEATURE:
<223> OTHER INFORMATION: synthetic peptide

<400> SEQUENCE: 3

Glu Thr Arg
1

<210> SEQ ID NO 4
<211> LENGTH: 3
<212> TYPE: PRT
<213> ORGANISM: artificial sequence
<220> FEATURE:
<223> OTHER INFORMATION: synthetic peptide

<400> SEQUENCE: 4

Asp Asn Asp
1

<210> SEQ ID NO 5
<211> LENGTH: 12
<212> TYPE: PRT
<213> ORGANISM: artificial sequence
<220> FEATURE:
<223> OTHER INFORMATION: synthetic peptide

<400> SEQUENCE: 5

Gly Gly Tyr Asp Ser Ser Ala Gly Tyr Ala Gly Met
1               5                   10

<210> SEQ ID NO 6
```

```
<211> LENGTH: 11
<212> TYPE: PRT
<213> ORGANISM: artificial sequence
<220> FEATURE:
<223> OTHER INFORMATION: synthetic peptide

<400> SEQUENCE: 6

Gly Ser Tyr Asp Arg Ser Gly Gly Val Gly Thr
1               5                   10

<210> SEQ ID NO 7
<211> LENGTH: 8
<212> TYPE: PRT
<213> ORGANISM: artificial sequence
<220> FEATURE:
<223> OTHER INFORMATION: synthetic peptide

<400> SEQUENCE: 7

Gly Phe Asp Phe Ser Ser His Gly
1               5

<210> SEQ ID NO 8
<211> LENGTH: 8
<212> TYPE: PRT
<213> ORGANISM: artificial sequence
<220> FEATURE:
<223> OTHER INFORMATION: synthetic peptide

<400> SEQUENCE: 8

Gly Phe Thr Leu Ser Ser Tyr Gly
1               5

<210> SEQ ID NO 9
<211> LENGTH: 8
<212> TYPE: PRT
<213> ORGANISM: artificial sequence
<220> FEATURE:
<223> OTHER INFORMATION: synthetic peptide

<400> SEQUENCE: 9

Ile Ser Gly Ser Gly Ser Gly Thr
1               5

<210> SEQ ID NO 10
<211> LENGTH: 8
<212> TYPE: PRT
<213> ORGANISM: artificial sequence
<220> FEATURE:
<223> OTHER INFORMATION: synthetic peptide

<400> SEQUENCE: 10

Ile Arg Ser Asp Gly Ser Asn Thr
1               5

<210> SEQ ID NO 11
<211> LENGTH: 14
<212> TYPE: PRT
<213> ORGANISM: artificial sequence
<220> FEATURE:
<223> OTHER INFORMATION: synthetic peptide

<400> SEQUENCE: 11

Val Arg Thr Arg Gly Ser Phe Asn Ile Val Thr Ile Asp Thr
1               5                   10

<210> SEQ ID NO 12
<211> LENGTH: 16
```

<212> TYPE: PRT
<213> ORGANISM: artificial sequence
<220> FEATURE:
<223> OTHER INFORMATION: synthetic peptide

<400> SEQUENCE: 12

Ala Lys Ser Ala Tyr Gly Thr Gly Tyr Ser Ser Gly Arg Ile Asp Thr
1               5                   10                  15

<210> SEQ ID NO 13
<211> LENGTH: 106
<212> TYPE: PRT
<213> ORGANISM: artificial sequence
<220> FEATURE:
<223> OTHER INFORMATION: synthetic polypeptide

<400> SEQUENCE: 13

Leu Thr Gln Pro Ser Ser Val Ser Ala Asn Leu Gly Glu Thr Val Lys
1               5                   10                  15

Ile Thr Cys Ser Gly Gly Gly Asn Asp Lys Tyr Tyr Gly Trp Phe Gln
                20                  25                  30

Gln Lys Ser Pro Gly Ser Ala Pro Val Thr Val Ile Tyr Glu Thr Arg
        35                  40                  45

Ser Arg Pro Ser Asp Ile Pro Ser Arg Phe Ser Gly Ser Lys Ser Gly
    50                  55                  60

Ser Thr Ala Thr Leu Thr Ile Thr Gly Val Gln Ala Glu Asp Glu Ala
65                  70                  75                  80

Val Tyr Phe Cys Gly Gly Tyr Asp Ser Ser Ala Gly Tyr Ala Gly Met
                85                  90                  95

Phe Gly Ala Gly Thr Thr Leu Thr Val Leu
            100                 105

<210> SEQ ID NO 14
<211> LENGTH: 103
<212> TYPE: PRT
<213> ORGANISM: artificial sequence
<220> FEATURE:
<223> OTHER INFORMATION: synthetic polypeptide

<400> SEQUENCE: 14

Leu Thr Gln Pro Ser Ser Val Ser Ala Asn Pro Gly Glu Thr Val Lys
1               5                   10                  15

Ile Thr Cys Ser Gly Gly Ser Gly Arg Tyr Gly Trp Phe Gln Gln Lys
                20                  25                  30

Ser Pro Gly Thr Ala Pro Val Thr Met Ile Tyr Asp Asn Asp Lys Arg
        35                  40                  45

Pro Ser Gly Ile Pro Pro Arg Phe Ser Gly Ser Thr Ser Gly Ser Thr
    50                  55                  60

Gly Thr Leu Ile Ile Thr Gly Val Gln Val Glu Asp Glu Ala Val Tyr
65                  70                  75                  80

Phe Cys Gly Ser Tyr Asp Arg Ser Gly Gly Val Gly Thr Phe Gly Ala
                85                  90                  95

Gly Thr Thr Leu Thr Val Leu
            100

<210> SEQ ID NO 15
<211> LENGTH: 131
<212> TYPE: PRT
<213> ORGANISM: artificial sequence
<220> FEATURE:
<223> OTHER INFORMATION: synthetic polypeptide

```
<400> SEQUENCE: 15

Thr Val Thr Leu Asp Glu Ser Gly Gly Gly Leu Gln Thr Pro Gly Gly
1               5                   10                  15

Ala Val Ser Leu Val Cys Lys Ala Ser Gly Phe Asp Phe Ser Ser His
            20                  25                  30

Gly Met Gly Trp Val Arg Gln Ala Pro Gly Lys Gly Leu Glu Trp Val
        35                  40                  45

Ala Gly Ile Ser Gly Ser Ser Gly Thr Gly Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asp Leu Arg Pro Glu Asp Thr Ala Thr Tyr Tyr Cys
                85                  90                  95

Val Arg Asp Val Arg Thr Arg Gly Ser Phe Asn Ile Val Thr Ile Asp
                100                 105                 110

Thr Trp Gly His Gly Thr Glu Val Ile Val Ser Ser Ser Gly Gln
            115                 120                 125

Ala Gly Gln
    130

<210> SEQ ID NO 16
<211> LENGTH: 130
<212> TYPE: PRT
<213> ORGANISM: artificial sequence
<220> FEATURE:
<223> OTHER INFORMATION: synthetic polypeptide

<400> SEQUENCE: 16

Thr Val Thr Leu Asp Glu Ser Gly Gly Gly Leu His Thr Pro Gly Gly
1               5                   10                  15

Ala Leu Ser Leu Val Cys Lys Ala Ser Gly Phe Thr Leu Ser Ser Tyr
            20                  25                  30

Gly Met Phe Trp Val Arg Gln Ala Pro Gly Lys Gly Leu Glu Phe Val
        35                  40                  45

Ala Tyr Ile Arg Ser Asp Gly Ser Asn Thr Tyr Tyr Gly Ala Ala Val
    50                  55                  60

Lys Gly Arg Ala Thr Ile Ser Arg Asp Asp Gly Gln Ser Thr Val Arg
65                  70                  75                  80

Leu Gln Leu Asn Asn Leu Arg Ala Glu Asp Thr Gly Ile Tyr Phe Cys
                85                  90                  95

Ala Lys Ser Ala Tyr Gly Thr Gly Tyr Ser Ser Gly Arg Ile Asp Thr
                100                 105                 110

Trp Gly His Gly Thr Glu Val Ile Val Ser Ser Thr Ser Gly Gln Ala
            115                 120                 125

Gly Gln
    130
```

ANTI-EGF LIKE DOMAIN MULTIPLE 6 (EGFL6) ANTIBODIES

This application is a 371 National Phase Application of International Application No. PCT/CN2018/108427, filed Sep. 28, 2018, which claims benefit of priority to U.S. Provisional Application No. 62/566,509, filed Oct. 1, 2017, the entirety of both of which are referenced herein.

FIELD OF THE INVENTION

The invention relates to the field of cancer detection (or diagnosis) and treatment. Particularly, the invention relates to anti-EGF like domain multiple 6 antibody (anti-EGFL6 antibody) and cancer detection (or diagnosis) and treatment using the anti-EGFL6 antibody.

BACKGROUND OF THE INVENTION

Cancer is the uncontrolled growth of abnormal cells anywhere in a body. The abnormal cells are termed cancer cells, malignant cells, or tumor cells. Early diagnosis of a cancer often increases the likelihood of successful treatment or cure of such disease.

A biomarker is a potential tool in the detection of a cancer. EGFL6 is a member of the epidermal growth factor (EGF) repeat superfamily proteins and consists of an EGF-like repeat region and an integrin association motif (RGD). EGFL6 promotes endothelial cell migration and angiogenesis. George Yeung et al. report that EGFL6 encodes a predicted signal peptide, suggesting that it is secreted, and that its transcripts are expressed in brain and lung tumor and fetal tissues (George Yeung et al., Genomics 62, 1999, pp. 304-307). A study is conducted to identify the molecule profile of ovarian tumor vasculature showed that tumor vascular markers may serve as potential biomarkers and molecular targets for ovarian cancer, wherein EGFL6 is one of the markers (Ronald J. Buckanovich et al., Journal of Clinical Oncology, 2007, Vol. 25, No. 7, pp. 852-861). However, an article reports that EGFL6 mRNA was found in high levels in ovarian cancer, comparable to that in benign meningioma and when compared with fibroblastic meningioma, EGFL6 mRNA levels were significantly decreased in all other investigated tumors including glioma, lung cancer, hepatocellular carcinoma, pancreatic carcinoma, gastric cancer, breast cancer, prostate cancer, colorectal cancer and bladder cancer (Xuanchun Wang et al., PLOS ONE; 2012, Vol. 7, Issue 12, e52707).

It is also reported that EGFL6 is overexpressed in W1TR cell line and is a secreted protein that promotes endothelial cell migration and angiogenesis (Radoslaw Januchowski et al., Oncology Reports 32: 1981-1990, 2014). Another article reports that EGFL6 is a candidate tumor vasculature ligand in breast cancer (Benjimin M Larimer, J. Mol Biomark Diagn. 2014, 5(3): doi: 10.4172/2155-9929.1000178). WO2009057849 discloses a diagnostic composition for colon cancer, comprising an agent measuring mRNA or protein levels of one or more genes selected from KLK6, CKS2, IFITM1, SPP1, DPEP1, CST1, CDH3, ANLN, CXCL1, MELK, CDCA1, CTHRC1, CEACAM6, MMP1, LCN2, HS6ST2, EGFL6 and CA9.

However, no EGFL6 alone is actually applied in clinical cancer diagnosis. Moreover, there is also a need to develop an anti-EGFL6 antibody for cancer treatment.

SUMMARY OF THE INVENTION

The present disclosure provides an isolated anti-EGFL6 antibody or an antigen-binding portion thereof, comprising at least one of a light chain CDR1 (L-CDR1) consisting of the amino acid residue of SEQ ID NO: 1 or 2, or a variant having amino acid sequence with at least 80% identity to any of SEQ ID NOs: 1 and 2; a light chain CDR2 (L-CDR2) consisting of the amino acid residue of SEQ ID NO: 3 or 4, or a variant having amino acid sequence with at least 80% identity to any of SEQ ID NOs: 3 and 4; and a light chain CDR3 (L-CDR3) consisting of the amino acid residue SEQ ID NO: 5 or 6, or a variant having amino acid sequence with at least 80% identity to any of SEQ ID NOs: 5 and 6; and at least one of a heavy chain complementarity determining region 1 (H-CDR1) consisting of the amino acid residue of SEQ ID NO: 7 or 8, or a variant having amino acid sequence with at least 80% identity to any of SEQ ID NOs: 7 and 8; a heavy chain CDR2 (H-CDR2) consisting of the amino acid residue of SEQ ID NO: 9 or 10, or a variant having amino acid sequence with at least 80% identity to any of SEQ ID NOs: 9 and 10; and a heavy chain CDR3 (H-CDR3) consisting of the amino acid residue of SEQ ID NO: 11 or 12, or a variant having amino acid sequence with at least 80% identity to any of SEQ ID NOs: 11 and 12; such that said isolated antibody or antigen-binding portion thereof binds to EGFL6.

Certain embodiments of the antibody of the present disclosure include a monoclonal antibody, chimeric antibody, humanized antibody and human antibody. In some embodiments, the isolated anti-EGFL6 antibody is a single chain Fv (scFv), IgG, Fab, (Fab)$_2$, or (scFv')$_2$.

One embodiment of the present disclosure includes a light chain comprising an amino acid sequence having a sequence selected from the group consisting of SEQ ID NO: 13 or 14.

One embodiment of the present disclosure includes a heavy chain comprising an amino acid sequence having a sequence selected from the group consisting of SEQ ID NO: 15 or 16.

In a further embodiment, the invention comprises an isolated antibody (EL6_S12), comprising a light chain having an amino acid sequence as set forth in SEQ ID NO: 13 and a heavy chain having an amino acid sequence as set forth in SEQ ID NO: 15. In a further embodiment, the invention comprises an isolated antibody (EL6_E5), comprising a light chain having an amino acid sequence as set forth in SEQ ID NO: 14 and a heavy chain having an amino acid sequence as set forth in SEQ ID NO: 16.

The present disclosure provides a pharmaceutical composition comprising the anti-EGFL6 antibody of the present disclosure and a pharmaceutically acceptable carrier or excipient.

The present disclosure also provides a method for treating or preventing angiogenesis disorder in a subject, comprising administering an anti-EGFL6 antibody of the present disclosure to the subject.

The present disclosure also provides a method for inhibiting cancer cell growth or cancer metastasis in a subject comprising administering an anti-EGFL6 antibody of the present disclosure to the subject.

In some embodiments, each of the above identified compositions and methods of treatment may additionally include an additional anti-tumor drug and the administration of an additional one or more anti-tumor drug.

The present disclosure further provides a method for detecting or diagnosing a cancer or an elevated risk of future occurrence of a cancer, or predicting a metastasis or prognosis of a cancer in a subject, comprising contacting a biological sample from a subject with an anti-EGFL6 antibody of the present disclosure, quantifying the binding of EGFL6 antigen in the sample to the antibody, and comparing said binding to a reference value representing binding between the anti-EGFL6 antibody and the EGFL6 antigen determined in samples from control subjects not afflicted with a cancer.

The present disclosure further provides a method for monitoring the progression of a cancer in a subject already diagnosed with a cancer.

The present disclosure further provides a kit for detecting or diagnosing a cancer or an elevated risk of future occurrence of a cancer, or predicting a metastasis or prognosis of a cancer, or monitoring cancer progression in a subject, comprising an anti-EGFL6 antibody of the present disclosure.

DETAILED DESCRIPTION OF THE INVENTION

Figure 1:
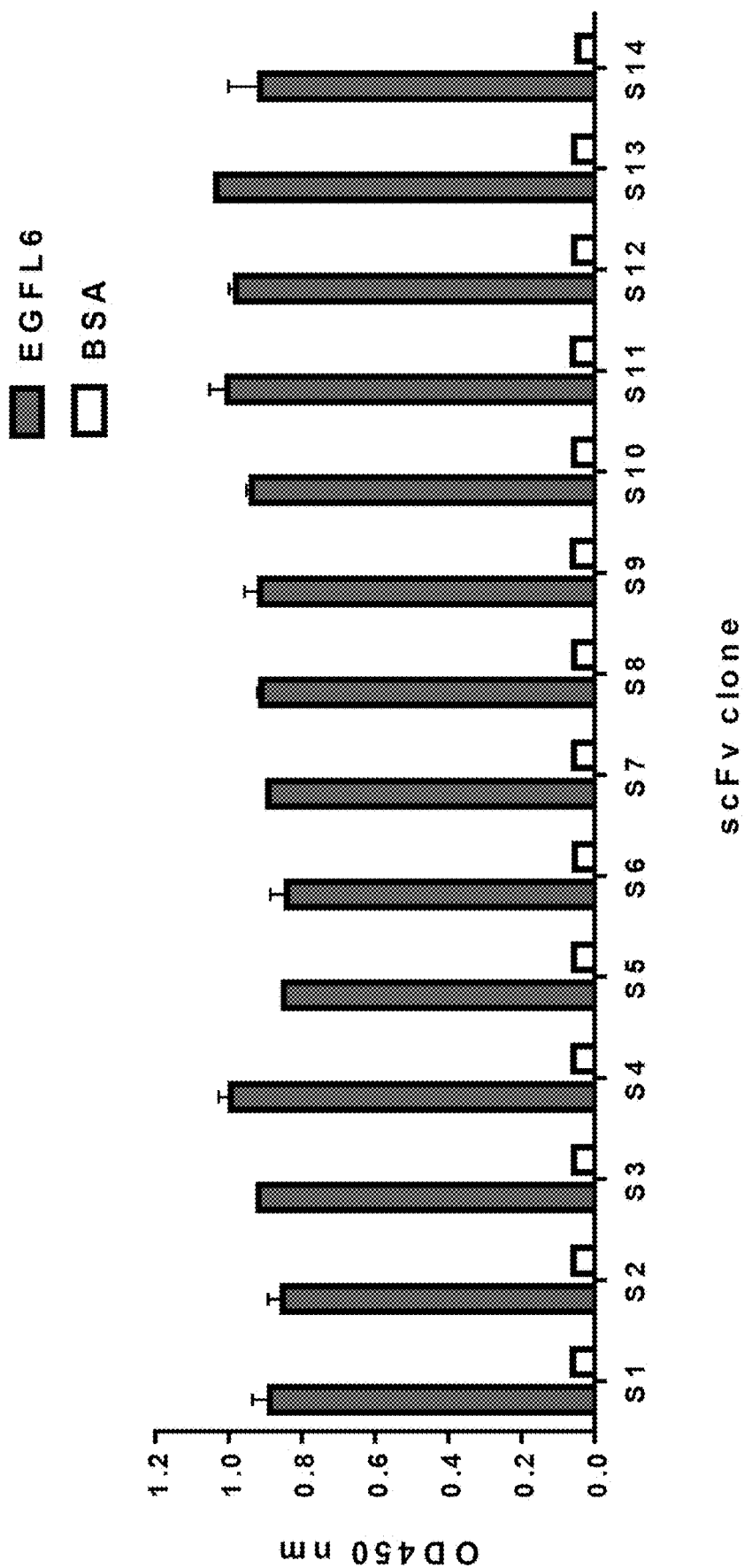
FIG. 1 shows the binding activity of anti-EGFL6 antibodies using ELISA.

The terminology herein is used to describe specific embodiments of the invention, but their usage does not delimit the invention, except as outlined in the claims. It is to be understood that both the foregoing general description and the following detailed description are examples and explanatory only and are not restrictive of the subject matter claimed in this application.

Terms such as "a", "an" and "the" are not intended to refer to only a singular entity, but include the general class of which a specific example may be used for illustration.

In this application, the use of "or" means "and/or" unless stated otherwise. Furthermore, use of the term "including" as well as other forms, such as "includes," and "included" is not limiting.

Definitions

As used herein, the terms "tumor," "cancer" and "carcinoma" are used interchangeably and refer to all neoplastic cell growth and proliferation, whether malignant or benign, and all pre-cancerous and cancerous cells and tissues.

As used herein, the term "marker" or "biomarker" are used interchangeably herein, and in the context of the present invention refer to a gene which is differentially expressed in a sample taken from a subject having a cancer as compared to a comparable sample taken from a control subject (e.g., a person with a negative diagnosis, normal or healthy subject).

As used herein, the term "biological sample" refers to a sample obtained from a patient. Biological samples, for example, can be obtained from blood, tissue (e.g. tumor), serum, stool, urine, sputum, cerebrospinal fluid, nipple aspirates and supernatant from cell lysate.

As used herein, the term "diagnostic" means identifying the presence or nature of a pathologic condition and includes identifying subjects who are at risk of developing a cancer. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is to measure the proportion of negatives that are correctly identified as such (e.g., the percentage of the subjects who are not diseased and are correctly identified as not having the condition).

As used herein, the terms "detection," "detecting" and the like, may be used in the context of detecting biomarkers, or of detecting a cancer (e.g. when positive assay results are obtained). In the latter context, "detecting" and "diagnosing" are considered synonymous.

A "test amount" of a marker refers to an amount of a marker present in a sample being tested.

A "control amount" of a marker can be any amount or a range of amount which is to be compared against a test amount of a marker.

The term "at risk of" is intended to mean at increased risk of, compared to a normal subject, or compared to a control group. Thus, a subject "at risk of" developing a cancer is at increased risk compared to a normal population, and a subject "at risk of" a recurrence of a cancer may be considered at increased risk of having a recurrence as compared to the risk of a recurrence among all treated cancer patients.

As used herein, the term "increased risk" or "elevated risk" mean any statistically significant increase in the probability, e.g., that the subject will develop a cancer, or a recurrence thereof.

As used herein, the term "prognosis" refers to the prediction of the likelihood of cancer-attributable death or progression, including recurrence, metastatic spread, and drug resistance, of a neoplastic disease, such as ovarian cancer. The term "poor prognosis" means that the prospect of survival and recovery of disease is unlikely despite the standard of care for the treatment of the cancer (for example, prostate cancer), that is, surgery, radiation, chemotherapy. Poor prognosis is the category of patients whose survival is less than that of the median survival.

As used herein, the term "metastasis" is defined as the spread of cancer from one part of the body to another. A tumor formed by cells that have spread is called a "metastatic tumor" or a "metastasis."

As used herein, the term "risk of metastasis" refers to a prognostic indication that the cancer in a particular patient, particularly a human patient, will advance to a metastatic state based on statistical predictors. Actual advance to a metastatic state is not required, and adoption of treatment modalities to try to delay or prevent the realization of such risk is anticipated to occur.

As used herein, the expression "reference value" refers to a laboratory value used as reference for the values/data obtained by means of samples obtained from a subject.

As used herein, "determination of a level", "determining a level" or "measuring a level" typically refer to calculation of an amount or concentration of a particular substance, or to quantifying an intensity of a signal from a probe that represents the amount or concentration of a particular substance.

As used herein, the term "antibody" is used in the broadest sense and specifically covers, for example, single monoclonal antibodies (including agonist, antagonist, and neutralizing antibodies), antibody compositions with polyepitopic specificity, polyclonal antibodies, single chain antiantibodies, and fragments of antibodies (see below) as long as they specifically bind a native polypeptide and/or exhibit a biological activity or immunological activity of the present invention. According to one embodiment, the antibody binds to an oligomeric form of a target protein, e.g., a trimeric form. The phrase "functional fragment or analog" of an antibody is a compound having a qualitative biological activity in common with an antibody to which it is being referred. For example, a functional fragment or analog of an antibody of this invention can be one which can specifically bind to EGFR. In one embodiment, the antibody can prevent or substantially reduce the ability of an EGFR to induce cell proliferation.

As used herein, the term "isolated antibody" is one which has been identified and separated and/or recovered from a component of its natural environment. Contaminant components of its natural environment are materials which would interfere with diagnostic or therapeutic uses for the antibody, and can include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN (DNASTAR) software. Those skilled in the art can determine appropriate parameters for measuring alignment, including any algorithms known in the art needed to achieve maximal alignment over the full length of the sequences being compared.

As used herein, the term "Fab" indicates an antigen binding fragment of an Ig (regardless of how prepared) including variable domain and first constant domain.

As used herein, the term "Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

As used herein, the term "single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains, which enables the sFv to form the desired structure for antigen binding. For a review of the sFv, see Pluckthun in The Pharmacology of Monoclonal Antibodies, vol. 113, Rosenburg and Moore eds., Springer-Verlag, New York, pp. 269-315 (1994).

As used herein, the term "complementarity determining region" (CDR) refers to the non-contiguous antigen combining sites found within the variable region of both heavy and light chain polypeptides. CDRs have been described by Kabat et al., J. Biol. Chem. 252: 6609-6616 (1977); Kabat et al., U.S. Dept. of Health and Human Services, "Sequences of proteins of immunological interest" (1991); by Chothia et al., J. Mol. Biol. 196: 901-917 (1987); and MacCallum et al., J. Mol. Biol. 262: 732-745 (1996), where the definitions include overlapping or subsets of amino acid residues when compared against each other.

As used herein, the term "humanized antibody" refers to a recombinant protein in which the CDRs from an antibody from one species; e.g., a murine or a chicken antibody, are transferred from the heavy and light variable chains of the antibody from the species into human heavy and light variable domains (framework regions). The constant domains of the antibody molecule are derived from those of a human antibody. In some cases, specific residues of the framework region of the humanized antibody, particularly those that are touching or close to the CDR sequences, may be modified, for example replaced with the corresponding residues from the original murine, rodent, subhuman primate, or other antibody. The humanized antibody may be achieved by various methods including (a) grafting only the non-human CDRs onto human framework and constant regions with or without retention of critical framework residues, or (b) transplanting the entire non-human variable domains, but "cloaking" them with a human-like section by replacement of surface residues. Such methods as are useful in practicing the present invention include that disclosed in Padlan, Mol. Immunol., 31(3): 169-217 (1994).

As used herein, the term "chimeric antibody" refers to a recombinant protein that contains the variable domains of both the heavy and light antibody chains, including the complementarity determining regions (CDRs) of an antibody derived from one species, preferably a rodent antibody or a chicken antibody, more preferably a murine antibody, while the constant domains of the antibody molecule are derived from those of a human antibody.

As used herein, the term "treatment" or "treating" of a disease is an approach for obtaining beneficial or desired results including clinical results. For purposes of the present invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delaying or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods provided herein contemplate any one or more of these aspects of treatment.

As used herein, the term "administer" or "administration" refers to the act of injecting or otherwise physically delivering a substance as it exists outside the body (e.g., a formulation of the invention) into a patient, such as by mucosal, intradermal, intravenous, intramuscular delivery and/or any other method of physical delivery described herein or known in the art. When a disease, or a symptom thereof, is being treated, administration of the substance typically occurs after the onset of the disease or symptoms thereof. When a disease, or symptoms thereof, is being prevented, administration of the substance typically occurs before the onset of the disease or symptoms thereof.

As interchangeably used herein, the terms "individual," "subject," "host," and "patient," refer to a mammal, including, but not limited to, murines (rats, mice), non-human primates, humans, canines, felines, ungulates (e.g., equines, bovines, ovines, porcines, caprines), etc.

As used herein, the term "therapeutically effective amount" or "efficacious amount" refers to the amount of a subject anti-EGFL6 antibody that, when administered to a mammal or other subject for treating a disease, is sufficient to effect such treatment for the disease.

Anti-EGFL6 Antibodies and Their Applications in Cancer Treatment

The present invention creates anti-EGFL6 antibodies, particularly, a single-chain antibody fragments (scFv) and humanized antibody, which have ability in binding to EGFL6 and in inhibiting angiogenesis and cancer cell growth.

In another aspect, the present invention provides an isolated anti-EGFL6 antibody or an antigen-binding portion thereof, comprising at least one of a light chain CDR1 (L-CDR1) consisting of the amino acid residue of SEQ ID NO: 1 or 2, or a variant having amino acid sequence with at least 80% identity to any of SEQ ID NOs: 1 and 2; a light chain CDR2 (L-CDR2) consisting of the amino acid residue of SEQ ID NO: 3 or 4, or a variant having amino acid sequence with at least 80% identity to any of SEQ ID NOs: 3 and 4; and a light chain CDR3 (L-CDR3) consisting of the amino acid residue SEQ ID NO: 5 or 6, or a variant having amino acid sequence with at least 80% identity to any of SEQ ID NOs: 5 and 6; and at least one of a heavy chain complementarity determining region 1 (H-CDR1) consisting of the amino acid residue of SEQ ID NO: 7 or 8, or a variant having amino acid sequence with at least 80% identity to any of SEQ ID NOs: 7 and 8; a heavy chain CDR2 (H-CDR2) consisting of the amino acid residue of SEQ ID NO: 9 or 10, or a variant having amino acid sequence with at least 80% identity to any of SEQ ID NOs: 9 and 10; and a heavy chain CDR3 (H-CDR3) consisting of the amino acid residue of SEQ ID NO: 11 or 12, or a variant having amino acid sequence with at least 80% identity to any of SEQ ID NOs: 11 and 12; such that said isolated antibody or antigen-binding portion thereof binds to EGFL6. Preferably, the sequence identity as mentioned above is at least 81%, 82%, 83%, 84%, 85%, 86%, 87%, 88%, 89%, 90%, 91%, 92%, 93%, 94%, 95%, 96%, 97%, 98% or 99%.

The amino acid sequences of the complementarity determining regions in light chains and heavy chains and are listed below.

CDRs of Light Chain

| L-CDR1 | L-CDR2 | L-CDR3 |
|---|---|---|
| GNDKY (SEQ ID NO: 1) | ETR (SEQ ID NO: 3) | GGYDSSAGYAGM (SEQ ID NO: 5) |
| SGRYG (SEQ ID NO: 2) | DND (SEQ ID NO: 4) | GSYDRSGGVGT (SEQ ID NO: 6) |

CDRs of Heavy Chain

| H-CDR1 | H-CDR2 | H-CDR3 |
|---|---|---|
| GFDFSSHG (SEQ ID NO: 7) | ISGSGSGT (SEQ ID NO: 9) | VRTRGSFNIVTIDT (SEQ ID NO: 11) |
| GFTLSSYG (SEQ ID NO: 8) | IRSDGSNT (SEQ ID NO: 10) | AKSAYGTGYSSGRIDT (SEQ ID NO: 12) |

In some embodiments, the isolated anti-EGFL6 antibody is a monoclonal antibody, chimeric antibody, humanized antibody or human antibody. In some embodiments, the isolated anti-EGFL6 antibody is a single chain antibody (such as Fv (scFv), IgG, Fab, (Fab)$_2$, or (scFv')$_2$).

According to the invention, the embodiments of the amino acids of the light chains and the heavy chains and of the antibodies of the invention are listed below.

Embodiments of Amino Acid Sequences of Light chains

LTQPSSVSANLGETVKITCSGGGNDKYGWFQQKSPGSAPVTVIYETRSR
PSDIPSRFSGSKSGSTATLTITGVQAEDEAVYFCGGYDSSAGYAGMFGAG
TTLTVL
(SEQ ID NO: 13) (EL6_S12)

LTQPSSVSANPGETVKITCSGGSGRYGWFQQKSPGTAPVTMIY**DNDKRPS
GIPPRFSGSTSGSTGTLIITGVQVEDEAVYFCGSYDRSGGVGTFGAGTTL
TVL
(SEQ ID NO: 14) (EL6_E5)

| Embodiments of Amino Acid Sequences of Heavy Chains |
|---|
| TVTLDESGGGLQTPGGAVSLVCKASGFDFSSHGMGWVRQAPGKGLEWVAGISGSGSGTGYAPAVKGRATISRDNGQSTLRLQLNDLRPEDTATYYCVRDVRTRGSFNIVTIDTWGHGTEVIVSSTSGQAGQ (SEQ ID NO: 15) (EL6_S12) |
| TVTLDESGGGLHTPGGALSLVCKASGFTLSSYGMFWVRQAPGKGLEFVAYIRSDGSNTYYGAAVKGRATISRDDGQSTVRLQLNNLRAEDTGIYFCAKSAYGTGYSSGRIDTWGHGTEVIVSSTSGQAGQ (SEQ ID NO: 16) (EL6_E5) |

In some embodiments, the invention provides a light chain comprising an amino acid sequence having a sequence selected from the group consisting of SEQ ID NO: 13 or 14.

In some embodiments, the light chain comprises an amino acid sequence having the sequence as set forth in SEQ ID NO: 13 wherein the L-CDR1, L-CDR2 and L-CDR3 are replaced with SEQ ID NO: 2, SEQ ID NO: 4 and SEQ ID NO: 6, respectively. In another embodiment, the light chain comprises an amino acid sequence having the sequence as set forth in SEQ ID NO: 14 wherein the L-CDR1, L-CDR2 and L-CDR3 are replaced with SEQ ID NO: 1, SEQ ID NO: 3 and SEQ ID NO: 5, respectively.

In some embodiments, the invention provides a heavy chain comprising an amino acid sequence having a sequence selected from the group consisting of SEQ ID NO: 15 or 16.

In some embodiments, the heavy chain comprises an amino acid sequence having the sequence as set forth in SEQ ID NO: 15 wherein the H-CDR1, H-CDR2 and H-CDR3 are replaced with SEQ ID NO: 8, SEQ ID NO: 10 and SEQ ID NO: 12, respectively. In another embodiment, the heavy chain comprises an amino acid sequence having the sequence as set forth in SEQ ID NO: 16 wherein the H-CDR1, H-CDR2 and H-CDR3 are replaced with SEQ ID NO: 7, SEQ ID NO: 9 and SEQ ID NO: 11, respectively.

In further embodiments, the invention comprises an isolated antibody, comprising a light chain having an amino acid sequence as set forth in the sequence selected from the group consisting of SEQ ID NOs: 13 and 14, or a variant having at least 80% identity to any of SEQ ID NOs: 13 and 14, and (ii) a heavy chain having an amino acid sequence as set forth in the sequence selected from the group consisting of SEQ ID NOs: 15 and 16 or a variant having at least 80% identity to any of SEQ ID NOs: 15 to 16. Preferably, the sequence identity as mentioned above is at least 90%, 91%, 92%, 93%, 94%, 95%, 96%, 97%, 98% or 99%.

In a further embodiment, the invention comprises an isolated antibody (EL6 S12), comprising a light chain having an amino acid sequence as set forth in SEQ ID NO: 13 and a heavy chain having an amino acid sequence as set forth in SEQ ID NO: 15. In a further embodiment, the invention comprises an isolated antibody (EL6_E5), comprising a light chain having an amino acid sequence as set forth in SEQ ID NO: 14 and a heavy chain having an amino acid sequence as set forth in SEQ ID NO: 16. In a further embodiment, the invention comprises an isolated antibody, comprising a light chain having an amino acid sequence as set forth in SEQ ID NO: 13 and a heavy chain having an amino acid sequence as set forth in SEQ ID NO: 16. In a further embodiment, the invention comprises an isolated antibody, comprising a light chain having an amino acid sequence as set forth in SEQ ID NO: 14 and a heavy chain having an amino acid sequence as set forth in SEQ ID NO: 15.

Techniques for preparing monoclonal antibodies against virtually any target antigen are well known in the art. See, for example, Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice or chicken with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

Various techniques, such as production of chimeric or humanized antibodies, may involve procedures of antibody cloning and construction. The antigen-binding variable light chain and variable heavy chain sequences for an antibody of interest may be obtained by a variety of molecular cloning procedures, such as RT-PCR, 5'-RACE, and cDNA library screening. The variable heavy or light chain sequence genes of an antibody from a cell that expresses a murine antibody can be cloned by PCR amplification and sequenced. To confirm their authenticity, the cloned VL and VH genes can be expressed in cell culture as a chimeric antibody as described by Orlandi et al., (Proc. Natl. Acad. Sci., USA, 86: 3833 (1989)). Based on the variable heavy or light chain gene sequences, a humanized antibody can then be designed and constructed as described by Leung et al. (Mol. Immunol., 32: 1413 (1995)).

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13: 469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. Techniques for production of humanized monoclonal antibodies are well known in the art (see, e.g., Jones et al., 1986, Nature, 321: 522; Riechmann et al., Nature, 1988, 332: 323; Verhoeyen et al., 1988, Science, 239: 1534; Carter et al., 1992, Proc. Nat'l Acad. Sci. USA, 89: 4285; Sandhu, Crit. Rev. Biotech., 1992, 12: 437; Tempest et al., 1991, Biotechnology 9: 266; Singer et al., J. Immun., 1993, 150: 2844).

Phage display technology can be used to produce the anti-EGFL6 antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Curr. Opin Struct. Biol. 3: 564-571 (1993). Several sources of V-gene segments can be used for phage display. Clackson et al., Nature 352: 624-628 (1991) isolated a diverse array of anti-oxazolone antibodies from a small random combinatorial library of V genes derived from the spleens of immunized mice. In other embodiments, ribosome display technology can be used to produce the anti-EGFL6 antibodies and antibody fragments in vitro.

Various techniques have been developed for the production of antibody fragments. Traditionally, these fragments were derived via proteolytic digestion of intact antibodies. However, these fragments can now be produced directly by recombinant host-cells, for example, using nucleic acids encoding anti-EGFL6 antibodies of the present disclosure. Fab, Fv and scFv antibody fragments can all be expressed in and secreted from E. coli, thus allowing the straightforward production of large amounts of these fragments. Anti-EGFL6 antibody fragments can also be isolated from the antibody phage libraries as discussed above. Alternatively, Fab'-SH fragments can be directly recovered from E. coli and chemically coupled to form F(ab')$_2$ fragments. According to another approach, F(ab')$_2$ fragments can be isolated directly from recombinant host-cell culture. Production of Fab and F(ab')$_2$ antibody fragments with increased in vivo half-lives are described in U.S. Pat. No. 5,869,046. In other embodiments, the antibody of choice is a single chain Fv fragment (scFv).

Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the antibodies of the present disclosure can also be constructed in whole or in part using standard peptide synthesis well known in the art.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

In addition to recombinant methods, the antibodies and variants thereof that are disclosed herein can also be constructed in whole or in part using standard peptide synthesis. Solid phase synthesis of the polypeptides can be accomplished by attaching the C-terminal amino acid of the sequence to an insoluble support followed by sequential addition of the remaining amino acids in the sequence. Techniques for solid phase synthesis are described by Barany & Merrifield, The Peptides: Analysis, Synthesis, Biology. Vol. 2: Special Methods in Peptide Synthesis, Part A. pp. 3-284; Merrifield et al., J. Am. Chem. Soc. 85: 2149-2156, 1963, and Stewart et al., Solid Phase Peptide Synthesis, 2nd ed., Pierce Chem. Co., Rockford, Ill., 1984. Proteins of greater length may be synthesized by condensation of the amino and carboxyl termini of shorter fragments.

Pharmaceutical Compositions Comprising Anti-EDFL6 Antibody and Treatment or Prevention Applications of the Anti-EDFL6 Antibody Certain embodiments relate to a pharmaceutical composition comprising the anti-EGFL6 antibody of the invention and a pharmaceutically acceptable carrier or excipient. The term "pharmaceutically acceptable carrier" is intended to include, but not limited to, a non-toxic solid, semisolid or liquid filler, diluent, encapsulating material or formulation auxiliary of any type known to persons skilled in the art. Diluents, such as polyols, polyethylene glycol and dextrans, may be used to increase the biological half-life of the conjugate.

The pharmaceutical compositions of the present invention can be formulated according to conventional methods (for example, Remington's Pharmaceutical Science, latest edition, Mark Publishing Company, Easton, U.S.A.), and may also contain pharmaceutically acceptable carriers and additives. Examples include, but are not limited to, surfactants, excipients, coloring agents, flavoring agents, preservatives, stabilizers, buffers, suspension agents, isotonic agents, binders, disintegrants, lubricants, fluidity promoting agents, and corrigents, and other commonly used carriers can be suitably used. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, polyoxyethylene hardened castor oil 60, saccharose, carboxymethyl cellulose, corn starch, inorganic salt, and such.

An embodiment is directed to a method for treating or preventing angiogenesis disorder in a subject, comprising administering an anti-EGFL6 antibody of the present disclosure to the subject. Alternatively, an embodiment is directed to a use of an anti-EGFL6 antibody of the present disclosure in the manufacture of a medicament for treating or preventing angiogenesis disorder in a subject. A disorder characterized by pathological angiogenesis refers to a disorder where abnormal or aberrant angiogenesis, alone or in combination with others, contributes to causation, origination, or symptom of the disorder. Examples of this disorder include various cancers (e.g., vascularized tumors), eye disorders, inflammatory disorders, and others.

A further embodiment is directed to a method for inhibiting cancer cell growth or cancer metastasis in a subject comprising administering an anti-EGFL6 antibody of the present disclosure to the subject. Alternatively, a further embodiment is directed to a use of an anti-EGFL6 antibody of the present disclosure in the manufacture of a medicament for inhibiting cancer cell growth or cancer metastasis in a subject. Because angiogenesis is involved in both primary cancer growth and metastasis, the antiangiogenic treatment provided by the present disclosure is capable of inhibiting the cancer cell growth at the primary site as well as preventing metastasis of tumors at the secondary sites. Exemplary solid tumors include, but are not limited to, carcinomas of the skin, kidney, prostate, adipose tissue, lung, breast, bone, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, Kaposi's sarcoma, and sarcomas (such as gastrointestinal stromal tumor). In a further embodiment, the cancer is colorectal cancer, colon cancer or rectal cancer.

The present method also comprises administering the anti-EGFL6 antibody of the present disclosure concomitantly with, or subsequent to other standard therapies, wherein said standard therapy is selected from the group consisting of radiotherapy, surgery and chemotherapy.

In preferred embodiments, the subject is a mammal. Exemplary mammals include human, pig, sheep, goat, horse, mouse, dog, cat, cow, etc. Diseases that may be treated with the anti-EGFL6 antibody or a pharmaceutical composition thereof include cancer, such as cancer of the liver, skin, head and neck, lung, breast, prostate, ovaries, endometrium, cervix, colon, rectum, colon and rectum, bladder, brain, stomach, pancreas or lymphatic system. Preferably, the cancer is colorectal cancer.

The anti-EGFL6 antibody or the pharmaceutical composition thereof may be administered intravenously, intraperitoneally, intra-arterially, intra-thecally, intra-vesically, or intratumorally. One of ordinary skill will appreciate that effective amounts of the anti-EGFL6 antibody can be determined empirically. It will be understood that, when administered to a human patient, the total daily usage of the anti-EGFL6 antibody or composition will be decided by the attending physician within the scope of sound medical judgment. The specific therapeutically effective dose level for any particular patient will depend upon a variety of factors: the type and degree of the cellular response to be achieved; activity of the specific anti-EGFL6 antibody or composition employed; the age, body weight, general health, sex and diet of the patient; the time of administration, route of administration, and rate of excretion of the anti-EGFL6 antibody; the duration of the treatment; drugs used in combination or coincidental with the anti-EGFL6 antibody; and like factors well known in the medical arts.

Each of the above identified compositions and methods of treatment may additionally include an additional anti-tumor drug and the administration of an additional one or more anti-tumor drug. Anti-tumor drugs suitable for use with the present disclosure include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like. Examples of the additional anti-tumor drug include but are not limited to 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., temozolomide, dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-.alpha., etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); and 22) modulators of p53 protein function.

Detection or Diagnosis of Cancer Using Anti-EGFL6 Antibody

The present disclosure also shows that there is a connection between EGFL6 levels and cancer severity; accordingly, the expression of EGFL6 or a fragment thereof in high level in the biological sample as compared to a reference level of the expression of EGFL6 or a fragment thereof in the control sample is indicative of prediction of a metastasis or poor prognosis. The invention unexpectedly found that the anti-EGFL6 antibody of the present disclosure can be used as an indicator of a diagnosis or predication of a prognosis or an elevated risk of metastasis or future occurrence of a cancer in a subject. Accordingly, the present disclosure provides a method for detecting or diagnosing a cancer or an elevated risk of future occurrence of a cancer, or predicting a metastasis or prognosis of a cancer in a subject, comprising contacting a biological sample from a subject with an anti-EGFL6 antibody of the present disclosure, quantifying the binding of EGFL6 antigen in the sample to the antibody, and comparing said binding to a reference value representing binding between the anti-EGFL6 antibody and the EGFL6 antigen determined in samples from control subjects not afflicted with a cancer.

In one embodiment, the biological sample may be a cell, tissue, organ, organ sample, tissue biopsy, blood, plasma, serum, ascetic fluid, lymphocytes, urine, bone marrow fluid, lymphatic fluid, saliva, lachrymal fluid, mucosal fluid, amniotic fluid, or a combination thereof.

Detectable labels suitable for conjugation to antibodies and other binding reagents include radioisotopes, fluorescent labels, enzyme-substrate labels, chromogenic labels, chemiluminescent labels and colloidal gold particles.

Examples of the measurement method include, but are not limited to, a fluorescence immunoassay (FIA) method, an enzyme immunoassay (EIA) method, a radioimmunoassay (MA) method, a Western blotting method, dot blot, an immunohistochemical assay, Fluorescence Activated Cell Sorter (FACS), in vivo imaging and a radio-imaging assay.

The present disclosure further provides a method for monitoring the progression of a cancer in a subject already diagnosed with a cancer. In some embodiments, monitoring can be used to evaluate whether a particular treatment is successful.

In some embodiments, monitoring cancer progression comprises determining a first level of EGFL6 or a fragment thereof in a first biological sample obtained from a subject diagnosed with a cancer by the anti-EGFL6 antibody of the present disclosure; and determining a second level of EGFL6 or the fragment thereof in a second biological sample obtained from the subject by the anti-EGFL6 antibody of the present disclosure after a predetermined period of time; comparing the first and second levels of EGFL6 or the fragment thereof; wherein a higher level of EGFL6 or the fragment thereof in the second sample compared to the first sample is indicative of disease progression and worsening. Similarly, a lower level of EGFL6 or the fragment thereof in the second sample compared to the first sample is indicative of improvement.

The diagnostic methods of the present disclosure may be combined with the known diagnostic methods for a cancer.

Another aspect of the present disclosure encompasses a kit for detecting or diagnosing a cancer or an elevated risk of future occurrence of a cancer, or predicting a metastasis or prognosis of a cancer, or monitoring cancer progression in a subject. It is typically in a package which contains all elements, optionally including instructions. The package may be divided so that components are not mixed until desired. Individual components may be separately packaged within the kit. The kit may contain reagents necessary to detect the expression level of a marker gene. A kit is any manufacture (e.g., a package or container) comprising at least one reagent, e.g., an antibody reagent(s), for specifically detecting and/or measuring the expression level of a marker gene in a sample.

A variety of kits having different components are contemplated by the current disclosure. Generally speaking, the kit will include the means for quantifying EGFL6 or more biomarkers in a subject. In another embodiment, the kit will include means for collecting a biological sample, means for quantifying EGFL6 or more biomarkers in the biological sample, and instructions for use of the kit contents. In certain aspects, the kit comprises a means for quantifying the amount of a biomarker. In further aspects, the means for quantifying the amount of a biomarker comprises reagents necessary to detect the amount of a biomarker.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLE

Example 1 Construction of Anti-EGFL6 Single Chain Antibody Library and Biopanning Female white leghorn (Gallus domesticus) chickens were immunized with 50 ug of recombinant EGF6 in an equal volume of Freund's complete adjuvant by an intramuscular injection. Three additional immunizations with incomplete adjuvant were performed at intervals of 7 days. After each immunization, chicken IgY antibodies in egg yolk were collected and titrated by an enzyme-linked immunosorbent assay (ELISA) to determine the presence of humoral anti-EGFL6 antibody immune response. The egg yolk will be separated from the egg white for IgY purification using 10% Dextran sulphate according to published protocol (Akita, E. M., and Nakai, S. (1993). *Production and purification of Fab' fragments from chicken egg yolk immunoglobulin Y (IgY). J Immunol Methods* 162, 155-164).

The antibody libraries will be established based on the previous report (Andris-Widhopf, J., Rader, C., Steinberger, P., Fuller, R., and Barbas, C. F., 3rd (2000). *Methods for the generation of chicken monoclonal antibody fragments by phage display. J Immunol Methods* 242, 159-181. Barbas, C. F., 3rd, Kang, A. S., Lerner, R. A., and Benkovic, S. J. (1991). *Assembly of combinatorial antibody libraries on phage surfaces: the gene III site. Proc Natl Acad Sci USA* 88, 7978-7982). Briefly, chicken spleens were harvested and placed immediately in Trizol. Ten ug of total RNAs will be reversely transcribed into the first-strand cDNA. After amplification using chicken-specific primers, PCR products of heavy and light chain variable (VH and VL) regions with short or long linkers will be subjected to a second round of PCR, digested with SfiI and cloned into the pComb3X vector. Recombinant DNAs were transformed into *E. coli* ER2738 strain by electroporation. Recombinant phage was produced by the addition of VCS-M13 helper phage, precipitated with 4% polyethylglycol 8000 and 3% NaCl (w/v), re-suspended in phosphate-buffered saline (PBS) containing 1% bovine serum albumin (BSA). Then, $10^{11}$ plaque-forming units (pfu) of recombinant phages were added to wells pre-coated with EGFL6 protein (0.5 ug/well), and incubated at 37° C. for 2 h. Bound phages were eluted with 0.1 M HCl/glycine (pH 2.2)/0.1% BSA, neutralized with 2 M Tris base buffer and used to infect the ER2738 strain. The amplified phages were recovered as described above for the next round of selection. The panning procedure was repeated six times. The total DNAs were purified and transformed into TOP 10F' *E. coli* strain. Twenty clones were randomly selected and grown from the final panning process. Bacterial cells were lysed and analyzed for scFv antibody expression and binding reactivity to EGFL6. ScFv antibodies were purified using $Ni^{2+}$-charged sepharose as described by the manufacturer (Amersham Biosciences, UK). FIG. 1 shows the binding activity of anti-EGFL6 antibodies using ELISA. The total cell lysates of 14 clones randomly selected from each ELISA-positive phage library after the $6^{th}$ round of bio-panning were used to examine their anti-EGFL6 activity. It was found that most scFv antibodies can specifically bind to the EGFL6 protein (see FIG. 1).

Example 2 Binding Analysis of Anti-EGFL6 Single Chain Antibodies

Figure 2:
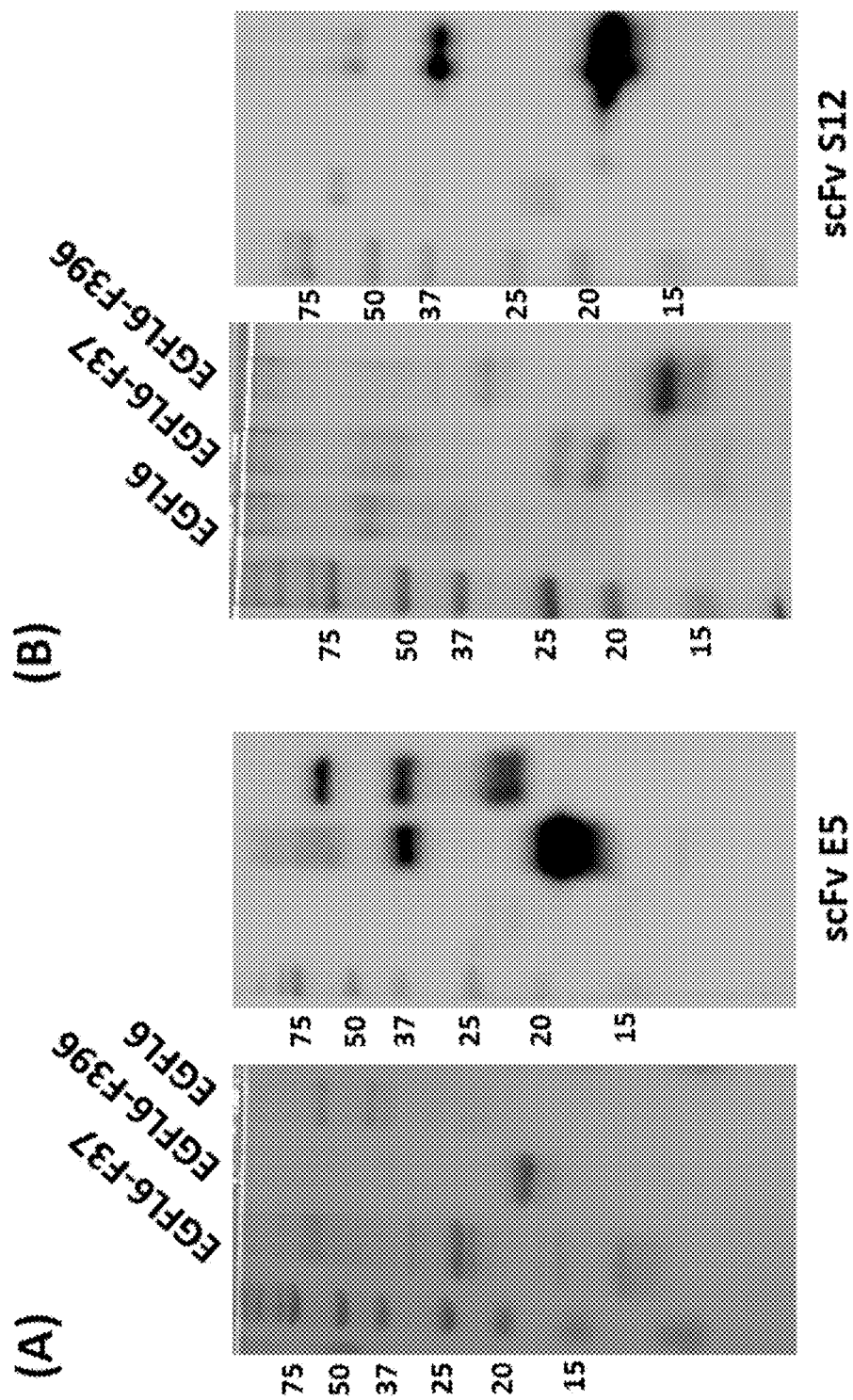
FIGS. 2A and 2B show full-length EGFL6 protein and EGFL6-F396 truncated fragment identified by E5 scFv (A) and S12 scFv (B) in the Western blotting.

The *E. coli*-expressed scFv antibodies were purified and incubated with the EGFL6 protein immobilized on nitrocellulose membranes. Their binding was subsequently detected by adding goat anti-chicken IgY light chain followed by HRP-conjugated donkey anti-goat Ig antibodies. After three washings, the membranes were developed with diaminobenzidine (DAB) substrate until the desired intensity was reached. FIG. 2 shows recombinant full-length EGFL6 protein (Lane EGFL6), and N-terminus truncated fragment (Lane EGFL6-F37) and the C-terminus truncated fragment (Lane EGFL6-F396) were used to SDS-PAGE analysis under reducing condition. FIGS. 2A and 2B show full-length EGFL6 protein and EGFL6-F396 truncated fragment identified by E5 scFv (FIG. 2A) and S12 scFv (FIG. 2B) in the Western blotting.

Example 3 Expression of EGFL6 in Serum of Colorectal Cancer Patients

Expressions of epidermal growth factor like protein 6 (EGFL6) were evaluated in the serum of cancer patients.

Figure 3:
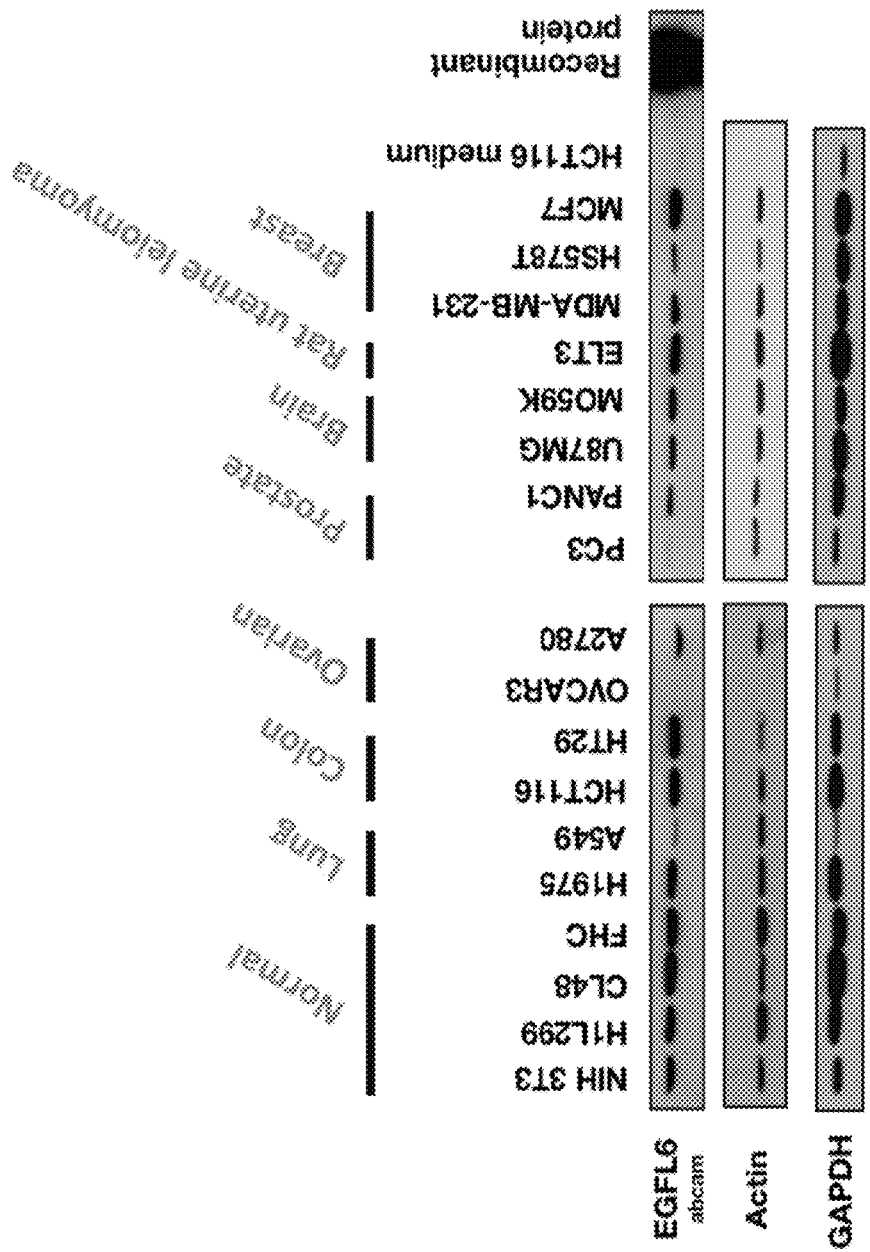
FIG. 3 shows a protein expression of EGFL6 in various cancer cell lines measured by Western Blot.

As shown in FIG. 3, a protein expression of EGFL6 in lung, colon, ovarian, prostate, brain, uterine and breast cancer cell lines was measured by Western Blot. These results suggest that EGFL6 could be found in patients with cancer and EGFL6 could serve as a cancer marker.

Figure 4:
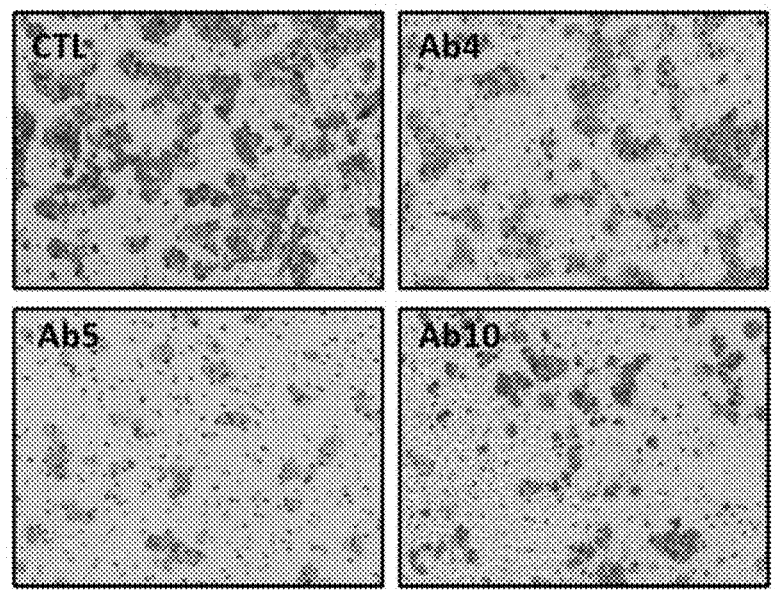
FIGS. 4 (A) and (B) show that the single chain antibodies Ab4, Ab5 (E5) and Ab10 were effective in inhibiting the cancer cells migrations (A) and the anti-EGFL6 single chain antibodies can effectively inhibit the formations of tumor capsule compared with the control group treated with the Paclitaxel (B).
Figure 4:
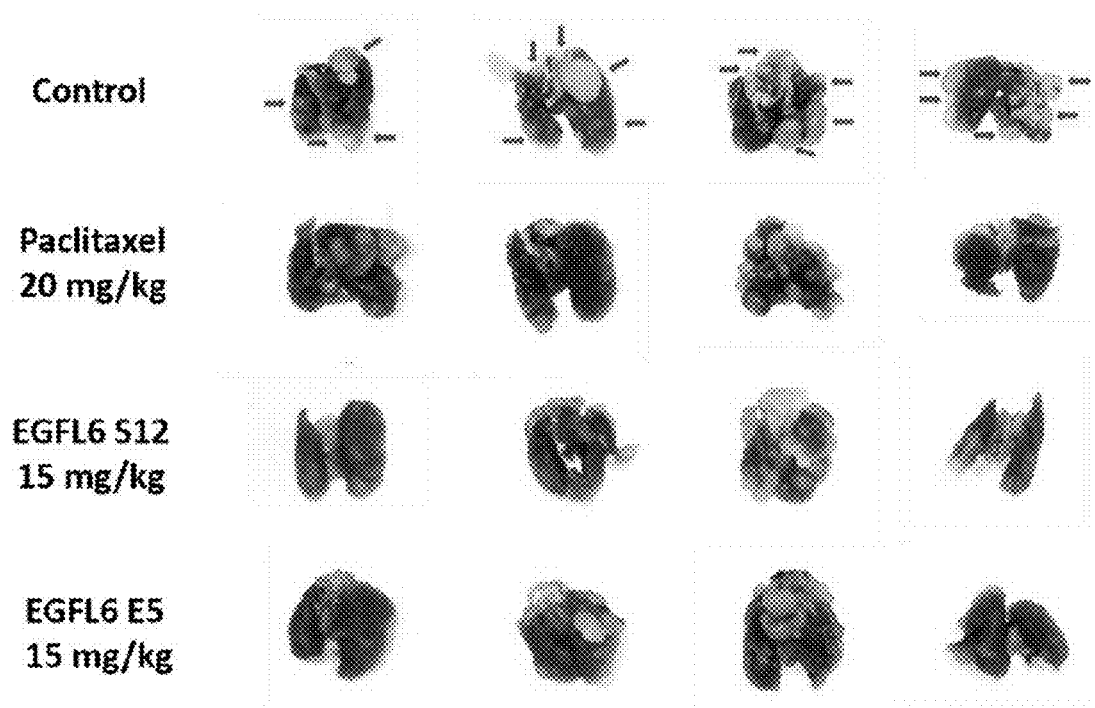

Example 4 Evaluation of Single Chain Antibody on Cell Migration Inhibition of Colorectal Cancer Cell Lines HCT116 and Inhibition of Cancer Metastasis by the Anti-EGFL6 Single Chain Antibodies S12 and E5 in Animal Model A cell penetration migration analysis was performed to evaluate the single chain antibodies for ability to inhibit cell migrations of the colorectal cancer cell lines HCT116. As shown in FIG. 4 (A), the anti-EGFL6 single chain antibodies were added to the colorectal cancer cell lines HCT116 and inhibit the growth of cancer cells under cell culture conditions. The results illustrated that the antibodies Ab4, Ab5 (E5) and Ab10 were effective in inhibiting the cancer cells migrations.

In a CT26 allograft mice model, the ability for inhibiting the metastasis of the colorectal cancer cells CT26 to lung was observed after the mice were administered with the anti-EGFL6 single chain antibodies (S12 and E5) and small molecule drug Paclitaxel. The anti-EGFL6 single chain antibodies S12 and E5 were administered with a dose of 15 mg/kg once every three days while the Paclitaxel was administered with a dose of 20 mg/kg once every four days. As shown in FIG. 4 (B), the groups treated with two of the anti-EGFL6 single chain antibodies at a dose of 15 mg/kg once every three days can effectively inhibit the formations of tumor capsule compared with the control group treated with the Paclitaxel at a dose of 20 mg/kg once every four days.

Example 5 Inhibition of Angiogenesis in Vivo by the Single Chain Antibodies E5 and S12

The five-week old nude mice were subcutaneously injected with 500 µl of matrigel mixed with EGF to induce angiogenesis. The nude mice were divided into four groups: (1) matrigel alone as the negative control group (Basal); (2) matrigel mixed with EGF (150 ng/mL) as the positive control group (Control); (3) the groups treated with the single chain antibody E5 at a dose of 15 mg/kg under EGF-induced condition and (4) the groups treated with the single chain antibody S12 at a dose of 15 mg/kg under EGF-induced condition. Each group had 3 nude mice and the single chain antibodies E5 and S12 were administered three times a week by the tail vein injection for one week. The nude mice were sacrificed on the eighth day. The matrix micelles in mice abdomen were removed and homogenized by the grinding rod, followed by measuring the hemoglobin contents.

Figure 5:
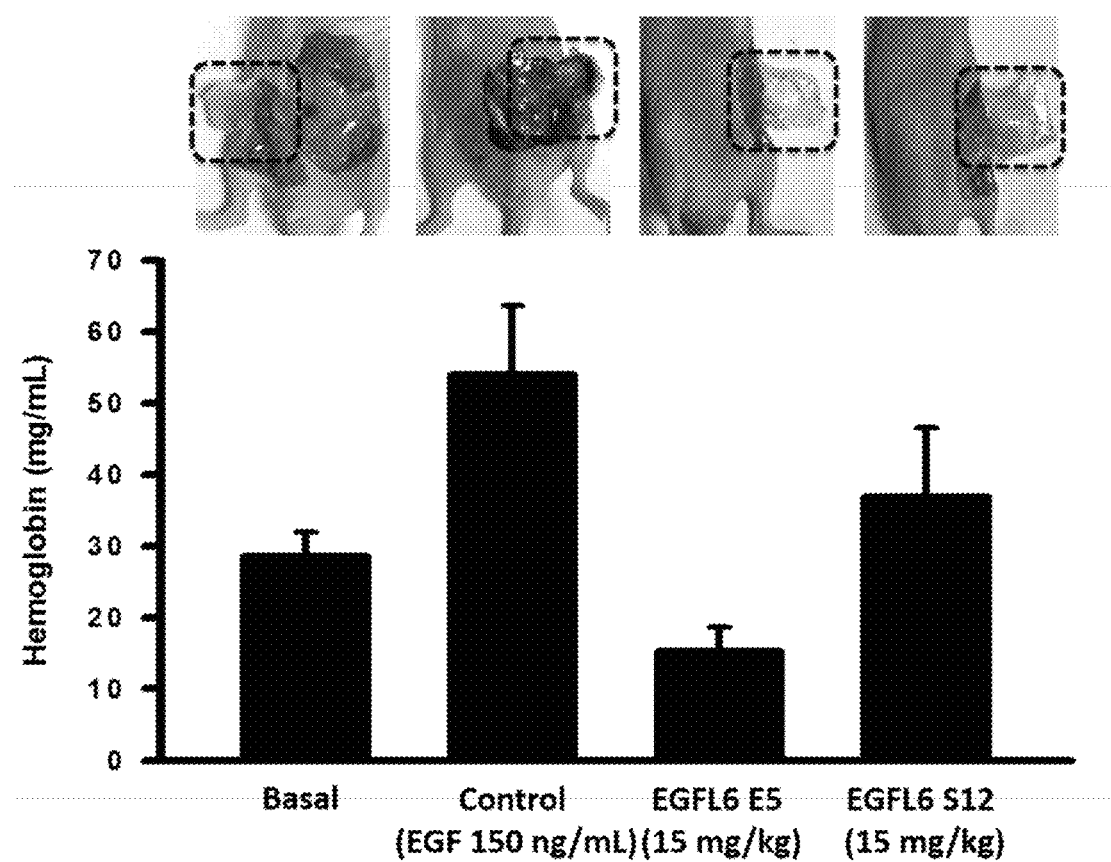
FIG. 5 shows the hemoglobin contents in the matrix micelles of the nude mice treated with the anti-EGFL6 single chain antibodies E5 and S12.

As shown in FIG. 5, the angiogenesis was not shown in the negative control group (Basal) injected with the matrigel alone. Comparing the negative control group (Basal), the angiogenesis was shown in the positive control group (Control) injected with the matrigel mixed with EGF after 24 hours. As shown in FIG. 5, it was apparent that the groups treated with both of the anti-EGFL6 single chain antibodies E5 and S12 showed the effects of inhibiting angiogenesis. In addition, the nude mice were sacrificed and the matrix micelles in mice abdomen were removed and the hemoglobin contents were measured. FIG. 5 illustrated that the hemoglobin contents in the matrix micelles of the nude mice treated with the anti-EGFL6 single chain antibodies E5 and S12 did show lower values correlated with the observation of the nude mice entity. In addition, as shown in FIG. 5, the anti-EGFL6 single chain antibodies E5 and S12 exhibited significant effects to inhibit angiogenesis. The hemoglobin contents of the groups treated with the anti-EGFL6 single chain antibodies E5 and S12 were almost equivalent to the contents of the negative control group (Basal). These results demonstrate that the anti-EGFL6 single chain antibodies E5 and S12 did have the ability of neutralizing EGFL6, and thus achieve the effects of inhibiting angiogenesis.

Example 6 Inhibition of Tumor Growth in Vivo by Anti-EGFL6 Humanized IgG Antibodies in Animal Model Humanization of variable regions of chicken scFv antibodies will be performed with the assistance of a molecular model generated by the algorithms applied in previous studies (Tsurushita et al., 2004; Zilber et al., 1990). In brief, the human V region framework used as an acceptor for the CDRs of the anti-EGFL6 scFv antibodies will be chosen based on sequence homology. Amino acid residues in the humanized V regions predicted from the three-dimensional model to be important for proper formation of the CDR structure will be substituted with the corresponding residues of chicken anti-EGFL6 scFv antibodies. Other methods will be combined and used to further fine-tune the structure of humanized anti-EGFL6 antibodies (Ewert et al., 2003; Sidhu et al., 2004).

Figure 6:
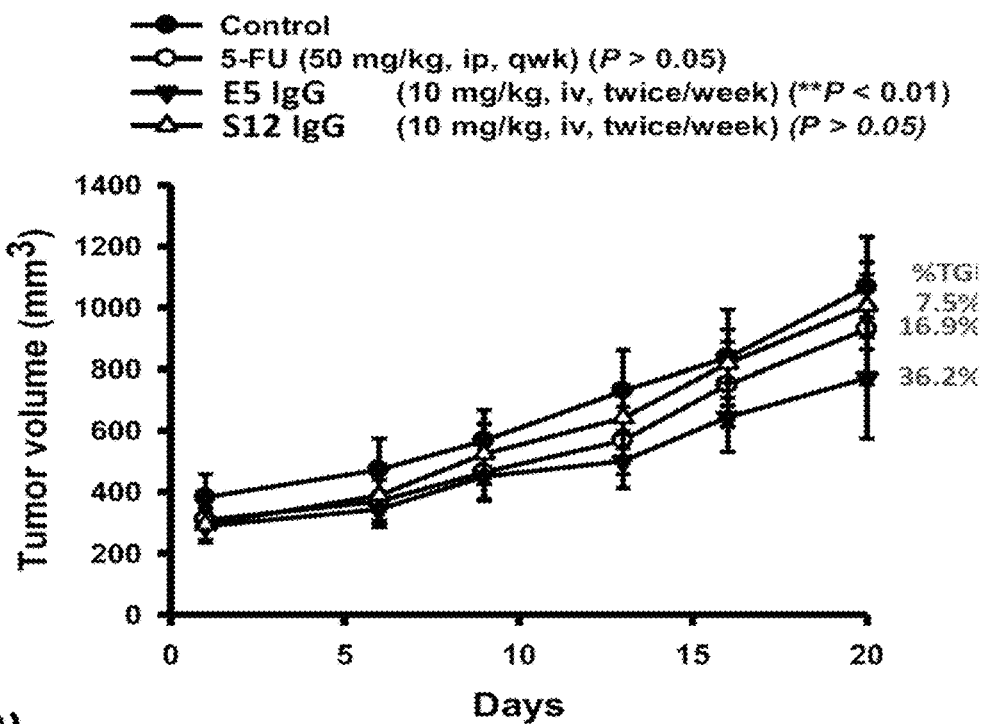
FIGS. 6 (A) and (B) shows that the humanized IgG antibodies S12 and/or E5 have the ability for inhibiting the tumor growth in colorectal cancer cell HCT-116 (A) and in non-small cell lung cancer A549 (B).
Figure 6:
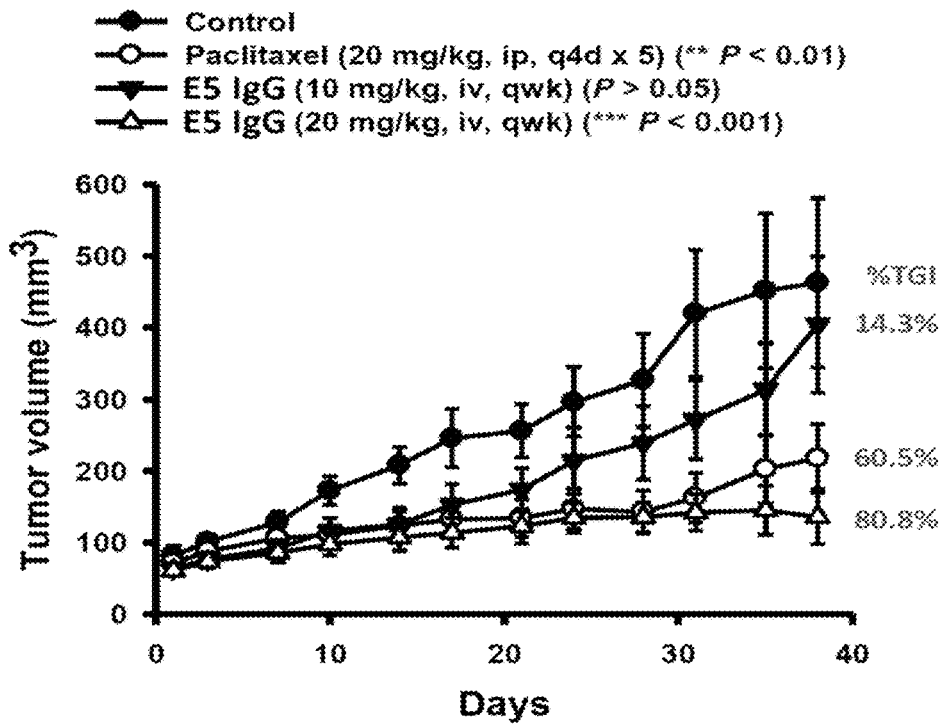

Two of the anti-EGFL6 humanized IgG antibodies (S12 and E5) were evaluated for their ability to inhibit the growth of the colorectal cancer cells HCT116, non-small cell lung cancer A549, triple negative breast cancer cell MDA-MB-231 and glioblastoma cancer cell U87 in xenograft mice. The mice were administered with indicated dose and intravenous injections twice a week. The initial tumor size was about 200 mm$^3$. After the end of the experiment, the ratio of tumor growth inhibition (% TGI) was calculated compared with the control group. As shown in FIG. 6 (A), both of the groups with the humanized IgG antibodies S12 and E5 have the ability to inhibit tumor growth (colorectal cancer cell HCT-116). The % TGI of the group with S12 antibody is 7.5% while the group with E5 antibody is 36.2%. As shown in FIG. 6 (B), the humanized IgG antibody E5 has the ability to inhibit tumor growth in non-small cell lung cancer A549. The % TGI of the group with E5 antibody (10 mg/kg) is 14.3% while the group with E5 antibody (20 mg/kg) is 80.8%.

Figure 7:
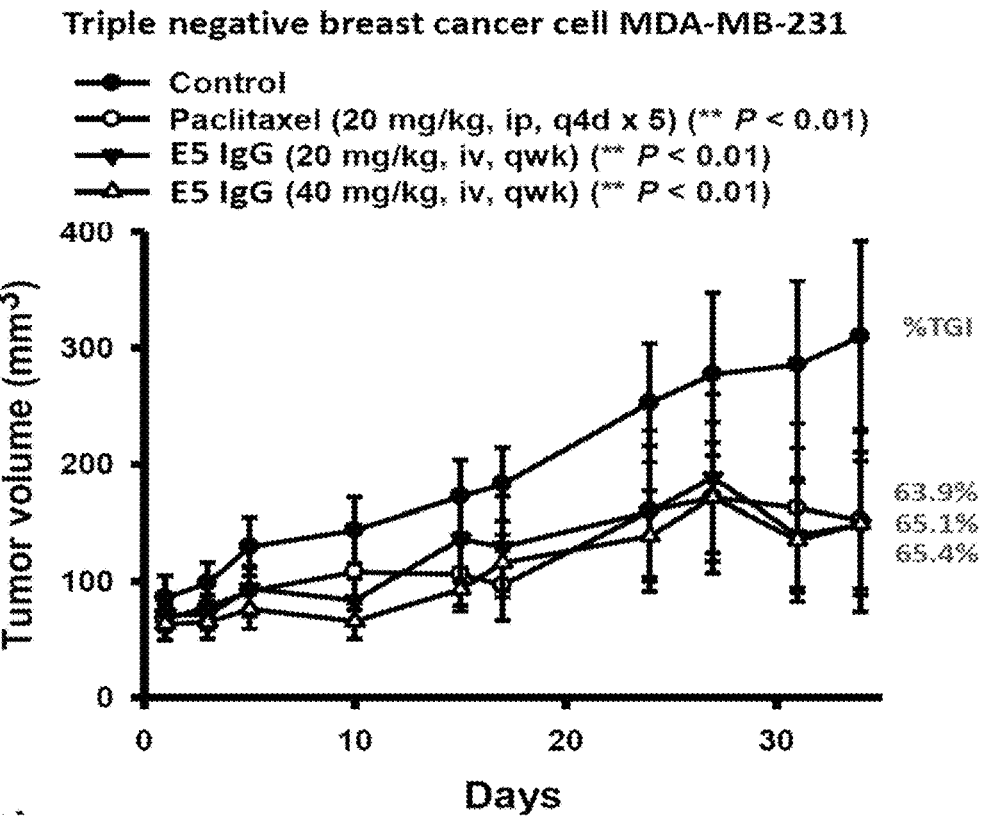
FIGS. 7 (A) and (B) shows that the humanized IgG antibody E5 has the ability for inhibiting the tumor growth in triple negative breast cancer cell MDA-MB-231(A) and glioblastoma cancer cell U87 (B).
Figure 7:
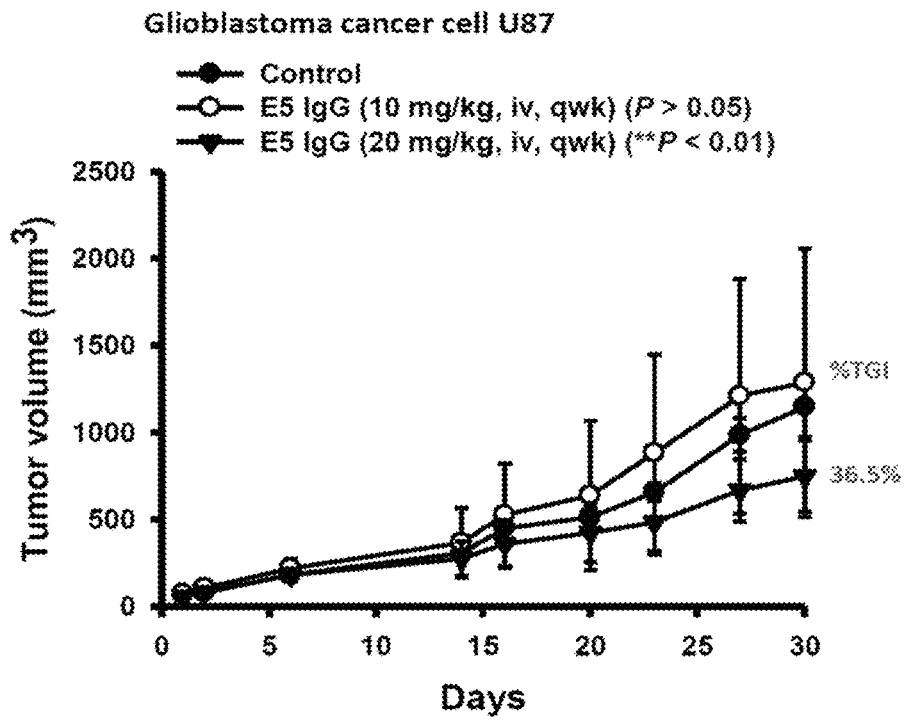

As shown in FIG. 7 (A), the groups with the humanized IgG antibody E5 have the ability for inhibiting the tumor growth (triple negative breast cancer cell MDA-MB-231). The % TGI of the group with E5 antibody (20 mg/kg) is 65.1% while the group with E5 antibody (40 mg/kg) is 65.4%. As shown in FIG. 7 (B), the groups with the single chain antibody E5 have the ability for inhibiting the tumor growth (glioblastoma cancer cell). The % TGI of the group with E5 antibody (20 mg/kg) is 36.5%.

Figure 8:
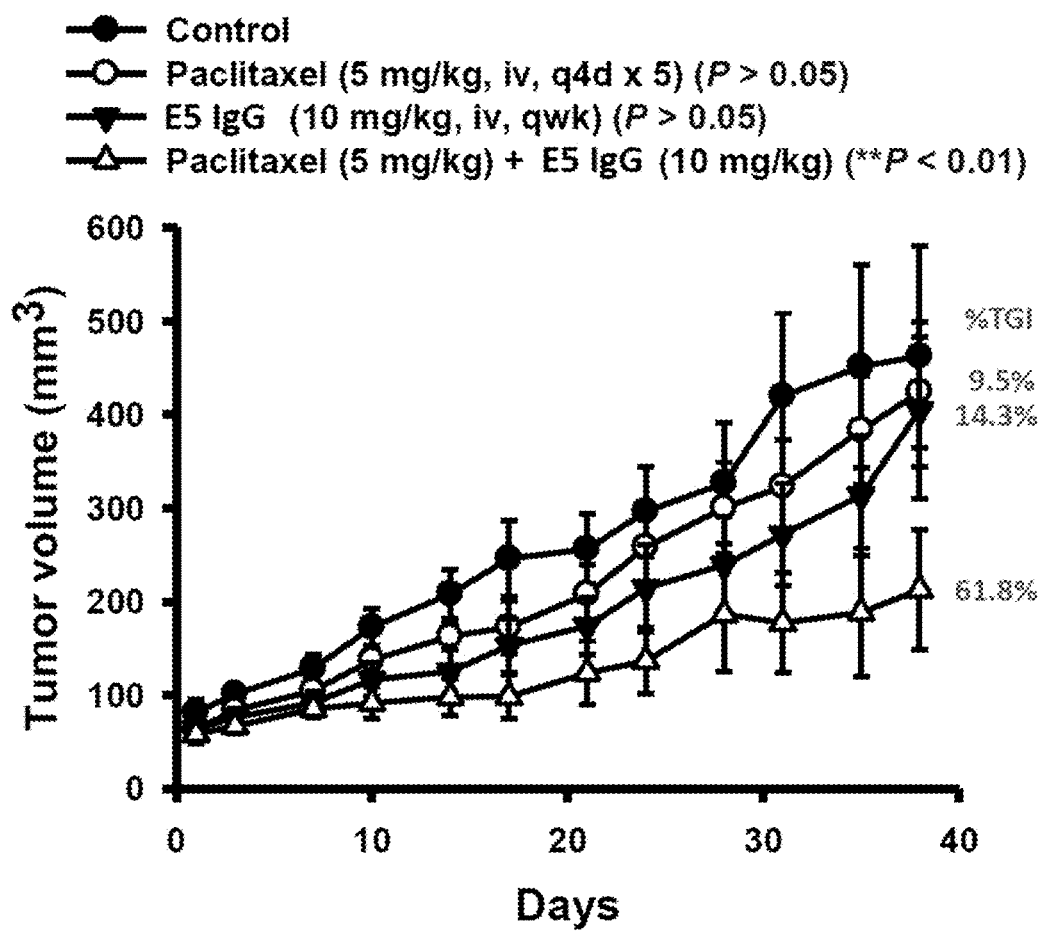
FIG. 8 shows the anti-cancer activity of humanized IgG antibody E5 combined with paclitaxel in human non-small cell lung cancer A549 xenograft model.

An anti-cancer activity of humanized IgG antibody E5 combined with paclitaxel in human non-small cell lung cancer A549 xenograft model was further conducted. Paclitaxel (5 mg/kg), E5 IgG (10 mg/kg) and paclitaxel (5 mg/kg) in combination with E5 IgG (10 mg/kg) were intravenously injected to mice. As shown in FIG. 8, the groups with the antibody E5 IgG have the ability for inhibiting the tumor growth and paclitaxel in combination with E5 IgG has an unexpected efficacy in inhibition of tumor. The % TGI of the group with E5 antibody (10 mg/kg) is 14.3%, while the group with paclitaxel in combination with E5 IgG is 61.8%.

What is claimed is:

1. An isolated anti-epidermal growth factor-like domain multiple 6 (anti-EGFL6) antibody or an antigen-binding portion thereof, comprising a light chain CDR1 (L-CDR1) having the amino acid sequence of SEQ ID NO: 2; a light chain CDR2 (L-CDR2) having the amino acid sequence of SEQ ID NO: 4; and a light chain CDR3 (L-CDR3) having the amino acid sequence of SEQ ID NO: 6; and
a heavy chain complementarity determining region 1 (H-CDR1) having the amino acid sequence of SEQ ID NO: 8; a heavy chain CDR2 (H-CDR2) having the amino acid sequence of SEQ ID NO: 10; and a heavy chain CDR3 (H-CDR3) having the amino acid sequence of SEQ ID NO: 12; such that said isolated antibody or antigen-binding portion thereof binds to EGFL6.

2. The anti-EGFL6 antibody or an antigen-binding portion thereof of claim 1, which is a monoclonal antibody, chimeric antibody, or humanized antibody.

3. The anti-EGFL6 antibody or an antigen-binding portion thereof of claim 1, which is a single chain Fv (scFv), IgG, Fab, (Fab)$_2$, or (scFv)$_2$.

4. The anti-EGFL6 antibody or an antigen-binding portion thereof of claim 1, which comprises a light chain having the amino acid sequence of SEQ ID NO: 14 and a heavy chain having the amino acid sequence of SEQ ID NO: 16.

5. A pharmaceutical composition comprising the anti-EGFL6 antibody or an antigen-binding portion thereof of claim 1 and a pharmaceutically acceptable carrier or excipient.

6. The pharmaceutical composition of claim 5, which further comprises an additional one or more anti-tumor drug.

* * * * *